(12) United States Patent
Kobetsky et al.

(10) Patent No.: US 8,302,276 B2
(45) Date of Patent: Nov. 6, 2012

(54) ANCHOR BOLT AND ANNULARLY GROOVED EXPANSION SLEEVE ASSEMBLY EXHIBITING HIGH PULL-OUT RESISTANCE, PARTICULARLY UNDER CRACKED CONCRETE TEST CONDITIONS

(75) Inventors: Robert G. Kobetsky, Chicago, IL (US); Michael Starozhitsky, Long Grove, IL (US); Matthew J. Reiter, Grayslake, IL (US); Donald Broomfield, Elgin, IL (US)

(73) Assignee: Illinois Tool Works Inc., Glenview, IL (US)

( * ) Notice: Subject to any disclaimer, the term of this patent is extended or adjusted under 35 U.S.C. 154(b) by 0 days.

(21) Appl. No.: 12/801,069

(22) Filed: May 20, 2010

(65) Prior Publication Data
US 2010/0229641 A1    Sep. 16, 2010

Related U.S. Application Data

(62) Division of application No. 11/598,025, filed on Nov. 13, 2006, now Pat. No. 7,811,037.

(60) Provisional application No. 60/810,627, filed on Jun. 5, 2006.

(51) Int. Cl.
*B23Q 17/00* (2006.01)
*F16B 13/06* (2006.01)

(52) U.S. Cl. ............... 29/407.08; 29/407.05; 29/407.01; 29/407.09

(58) Field of Classification Search .................. 411/57.1, 411/58, 60.1, 61, 69, 71–74; 29/407.01, 29/407.05, 407.08, 407.09
See application file for complete search history.

(56) References Cited

U.S. PATENT DOCUMENTS

| | | |
|---|---|---|
| 612,316 A | 10/1898 | Downes |
| 1,115,205 A | 10/1914 | Johnson |
| 1,164,322 A | 12/1915 | Yeatman |
| 1,470,858 A | 10/1923 | Maxwell |
| 1,604,762 A | 10/1926 | Slocum |
| 1,619,167 A | 3/1927 | Milton |

(Continued)

FOREIGN PATENT DOCUMENTS
DE              29917678          3/2000
(Continued)

OTHER PUBLICATIONS

Tin-Zinc Plating—Metal Finishing, Sep. 1995, pp. 10-15.

*Primary Examiner* — Essama Omgba
(74) *Attorney, Agent, or Firm* — Law Offices of Steven W. Weinrieb

(57) ABSTRACT

A wedge-type anchor assembly, capable of meeting cracked concrete testing standards, comprises an anchor bolt component and a substantially C-shaped expansion sleeve component annularly disposed about the anchor bolt component. A plurality of annular grooves, threads, or teeth are disposed only about the forward end portion of the expansion sleeve component, as opposed to throughout the entire axial length thereof, so that when the anchor bolt component is moved axially through the expansion sleeve component, the maximum interference area (M.I.A.) and maximum interference volume (M.I.V.) can be generated between the anchor bolt component and the expansion sleeve component in a controlled and predictable manner, as well as between the expansion sleeve component and the internal peripheral side wall portions of a concrete substrate or substructure can be generated so as to enhance pull-out resistance and reliability of the anchor assembly within the concrete substructure or substrate.

23 Claims, 8 Drawing Sheets

U.S. PATENT DOCUMENTS

| | | |
|---|---|---|
| 1,619,757 A | 3/1927 | Pelkey |
| 2,033,100 A | 3/1936 | Kellogg |
| 2,139,167 A | 12/1938 | Marshall |
| 2,626,023 A | 1/1953 | Lear |
| 3,438,659 A | 4/1969 | Waldron |
| 3,448,651 A | 6/1969 | Passer |
| 3,640,126 A * | 2/1972 | Te'eni ............................ 73/845 |
| 3,855,896 A | 12/1974 | Kaufman |
| 4,100,834 A | 7/1978 | Harris |
| 4,154,139 A | 5/1979 | Hage |
| 4,287,807 A | 9/1981 | Pacharis et al. |
| 4,330,230 A | 5/1982 | Giannuzzi |
| 4,403,894 A | 9/1983 | Clark |
| 4,482,277 A | 11/1984 | Schiefer |
| 4,518,290 A | 5/1985 | Frichmann et al. |
| 4,557,649 A | 12/1985 | Jeal |
| 4,636,123 A | 1/1987 | Herb |
| 4,640,654 A | 2/1987 | Fischer et al. |
| 4,657,456 A | 4/1987 | Anquetin |
| 4,720,224 A | 1/1988 | Peterken |
| 4,848,971 A | 7/1989 | Price Jr. |
| 4,854,793 A | 8/1989 | Ollivier et al. |
| 4,898,505 A | 2/1990 | Froehlich |
| 4,904,135 A | 2/1990 | Barthomeuf et al. |
| 4,929,134 A | 5/1990 | Bergner |
| 4,984,945 A | 1/1991 | Bergner |
| 5,017,067 A | 5/1991 | Ohlin |
| 5,193,957 A | 3/1993 | Fischer |
| 5,263,803 A | 11/1993 | Anquetin |
| 5,314,278 A | 5/1994 | Weber |
| 5,332,346 A | 7/1994 | Shinjo |
| 5,401,131 A | 3/1995 | Yoshino |
| 5,419,664 A | 5/1995 | Hengesbach et al. |
| 5,419,684 A | 5/1995 | Struble et al. |
| 5,429,882 A | 7/1995 | Carey, II et al. |
| 5,569,091 A | 10/1996 | Haage et al. |
| 5,685,678 A | 11/1997 | Giannuzzi et al. |
| 5,791,846 A | 8/1998 | Mayr |
| 5,816,760 A | 10/1998 | Mattner et al. |
| 5,911,550 A | 6/1999 | Popp |
| 5,993,128 A | 11/1999 | Mark et al. |
| 5,993,129 A | 11/1999 | Sato |
| 6,012,887 A | 1/2000 | Kaibach et al. |
| 6,062,784 A | 5/2000 | Wisser et al. |
| 6,213,697 B1 | 4/2001 | Uejima |
| 6,270,303 B1 | 8/2001 | Gauthier et al. |
| 6,308,544 B1 | 10/2001 | Kuehnl |
| 6,652,207 B2 | 11/2003 | Gauthier |
| 6,829,871 B1 | 12/2004 | McSherry et al. |
| 6,979,161 B2 | 12/2005 | Ando et al. |
| 7,722,772 B2 | 5/2010 | Furukawa et al. |
| 7,744,320 B2 * | 6/2010 | Kobetsky et al. ............ 411/60.1 |
| 7,811,037 B2 * | 10/2010 | Kobetsky et al. ............ 411/60.1 |
| 1,000,715 A1 | 8/2011 | Caywood |
| 2002/0054805 A1 | 5/2002 | Kaibach et al. |
| 2006/0150566 A1 | 7/2006 | Bakos |
| 2007/0277976 A1 | 12/2007 | Kobetsky et al. |

FOREIGN PATENT DOCUMENTS

| | | |
|---|---|---|
| DE | 10007626 | 8/2001 |
| DE | 10054618 | 5/2002 |
| DE | 10061808 | 6/2002 |
| DE | 10108844 | 9/2002 |
| DE | 20108139 | 9/2002 |
| DE | 10157586 | 6/2003 |
| EP | 0452573 | 10/1991 |
| EP | 0790414 | 2/1997 |
| EP | 0848169 | 6/1998 |
| EP | 0848170 | 6/1998 |
| EP | 0863318 | 9/1998 |
| EP | 0889250 | 1/1999 |
| EP | 0899468 | 3/1999 |
| EP | 0953777 | 11/1999 |
| EP | 1091134 | 2/2000 |
| EP | 1203889 | 5/2002 |
| EP | 1314897 | 5/2003 |
| EP | 1662156 | 5/2006 |
| FR | 1367502 | 7/1964 |
| GB | 723211 | 2/1955 |
| JP | 58-22505 | 8/1956 |
| JP | 53014264 | 2/1978 |
| JP | 8-82014 | 3/1996 |
| WO | WO 8601294 | 2/1986 |
| WO | WO 98/23871 | 6/1998 |
| WO | WO 2006/121301 | 11/2006 |

* cited by examiner

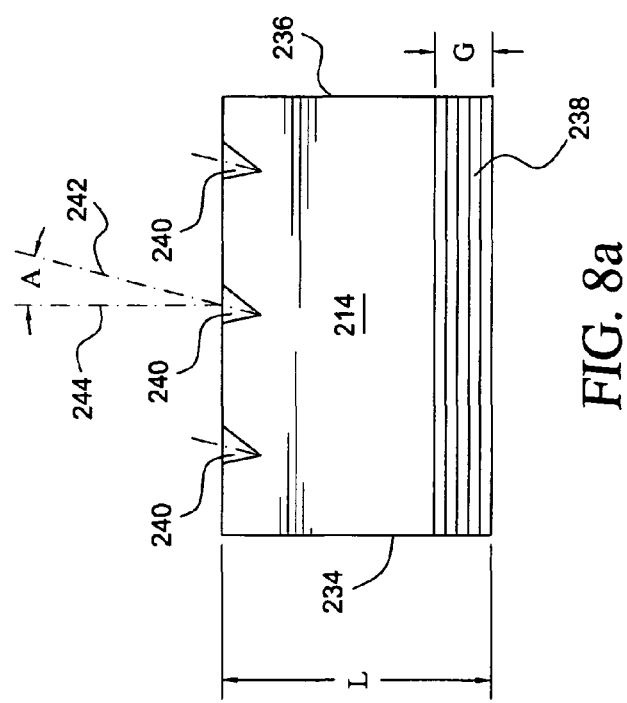

US 8,302,276 B2

ANCHOR BOLT AND ANNULARLY GROOVED EXPANSION SLEEVE ASSEMBLY EXHIBITING HIGH PULL-OUT RESISTANCE, PARTICULARLY UNDER CRACKED CONCRETE TEST CONDITIONS

CROSS-REFERENCE TO RELATED PATENT APPLICATION

This patent application is a divisional patent application of U.S. patent application Ser. No. 11/598,025, which was filed on Nov. 13, 2006, which is now U.S. Pat. No. 7,811,037, and which is related to, based upon, and effectively a utility patent application conversion from U.S. Provisional Patent Application Ser. No. 60/810,627, which was filed on Jun. 5, 2006, the filing date benefits of which are hereby incorporated by reference.

FIELD OF THE INVENTION

The present invention relates generally to wedge type anchors for use within concrete boreholes, and more particularly to a new and improved cracked concrete wedge type anchor assembly comprising an axially oriented anchor bolt and an annularly threaded or grooved expansion sleeve or clip annularly disposed around the axially oriented anchor bolt, wherein the annularly threaded or grooved expansion sleeve or clip has a continuous array of annularly oriented threads, grooves, or teeth, which comprises a predetermined number of threads, grooves, or teeth disposed about the forward external peripheral surface portion of the annularly threaded or grooved expansion sleeve or clip, and wherein the annularly threaded or grooved expansion sleeve or clip is fabricated from a metal sheet or plate and formed into the annularly threaded or grooved expansion sleeve or clip so as to have a substantially C-shaped cross-sectional configuration which enables the annularly threaded or grooved expansion sleeve or clip to be expanded by effectively being opened as the axially oriented anchor bolt is pulled therethrough.

The internal peripheral surface of the annularly grooved expansion sleeve or clip, within the leading end portion thereof, and the external peripheral surface of the axially oriented anchor bolt, within the leading end portion thereof, have predetermined inclined slopes, all of which features effectively combine and contribute to the achievement of the maximum interference area (M.I.A.) or the maximum interference volume (M.I.V.) as developed between the axially oriented anchor bolt and the annularly threaded or grooved expansion sleeve or clip so as to, in turn, develop the maximum interference area (M.I.A.) or the maximum interference volume (M.I.V.) between the annularly threaded or grooved expansion sleeve or clip and the internal peripheral side wall portions of a borehole formed within a concrete substrate or substructure so as to force the annularly threaded or grooved expansion sleeve or clip into its anchored disposition within the concrete borehole formed within the concrete substrate or substructure, and wherein further, each one of the annular threads, teeth, or grooves of the annularly threaded or grooved expansion sleeve or clip has a predetermined depth dimension so as to effectively ensure its engagement and retention within the side wall portions of the borehole despite any slight expansion or contraction of the concrete substrate or substructure.

BACKGROUND OF THE INVENTION

Anchoring assemblies, for use within boreholes that have been pre-drilled, for example, within concrete substructures or substrates, are of course well known in the art and industry. Examples of such anchoring assemblies are disclosed, for example, within U.S. Pat. No. 5,911,550 which issued to Popp et al. on Jun. 15, 1999, U.S. Pat. No. 4,929,134 which issued to Bergner on May 29, 1990, U.S. Pat. No. 4,904,135 which issued to Barthomeuf et al. on Feb. 27, 1990, U.S. Pat. No. 4,720,224 which issued to Peterken on Jan. 19, 1988, U.S. Pat. No. 1,115,205 which issued to Johnson on Oct. 27, 1914, and U.S. Pat. No. 1,000,715 which issued to Caywood on Aug. 15, 1911. Obviously, in connection with the use of such anchoring assemblies within the concrete substructures of substrates, it is desirable to develop and use anchoring assemblies wherein the same are characterized by means of structural components or features which will effectively ensure the fact that the holding capabilities, or the pull-out resistance characteristics, of the anchoring assemblies will not be compromised whereby the anchoring assemblies will remain solidly affixed, or stably embedded, within the concrete substrates or substructures for long periods of time despite the presence, existence, or development of various, varying, or volatile external environmental conditions. In this manner, not only will the anchoring assemblies exhibit desirably long service lives, but in addition, the structural components, which have been secured to the concrete substructures or substrates by means of such anchoring assemblies, will be solidly and reliably affixed or secured to the underlying concrete substrates or substructures.

One means for effectively determining or testing the performance capabilities of such anchoring assemblies comprises an industrially accepted operational technique known as cracked concrete testing which basically simulates real-world conditions, in a compressed time-frame, under laboratory testing conditions. In accordance with such operational testing, and with reference being made to FIG. 1, a block of concrete 10 has a plurality of transversely oriented rebars 12 fixedly embedded therein. A hydraulic pump 14 is operatively connected to each one of first end portions 16 of the plurality of rebars 12 by means of suitable hydraulic connectors 18, and crack initiators 20, which may comprise, for example, wedge-type devices, plates, hydraulic expansion tubes, or the like, are incorporated within the concrete block 10 at predetermined locations along the transverse extent of the concrete block 10 so as to effectively cause or initiate the development or propagation of longitudinally oriented cracks 22 within the concrete block 10, at a plurality of transversely spaced locations, when the hydraulic pump 14 is operatively cycled between pulling and pushing modes of operation whereby pulling and pushing forces are alternatively exerted upon the first end portions 16 of the rebars 12. In this manner, the rebars 12 effectively undergo expansion and contraction whereby, in turn, the cracks 22 are caused to be cyclically expanded or contracted between OPEN and CLOSED positions. A plurality of first linearly variable displacement transformers (LVDTs) 24 are operatively associated with each one of the longitudinally extending cracks 22 so as to in fact measure the size of each crack 22 as each one of the cracks 22 is cyclically expanded or contracted between its OPEN and CLOSED positions as a result of the exertion of the pulling and pushing forces upon the first end portions 16 of the rebars 12 by means of the hydraulic pump 14.

Continuing still further, and with reference being made to FIG. 2, when the pump 14 is operated so as to be disposed in its mode whereby pushing forces are exerted upon the first end portions 16 of the rebars 12 so as to effectively cause the cracks 22 to be disposed in their CLOSED positions, a hole 26 is drilled or bored within each one of the cracked regions 22 of the concrete block 10, and an anchor assembly 28 is installed within each one of the boreholes 26. Each one of the anchor assemblies 28 is subsequently torqued to its specifications, and a predetermined sustained load, as schematically illustrated by means of the arrow L, is then applied to each one of the anchor assemblies 28 by means of a suitable spring-loaded or hydraulic pump load assembly or bracket 30 that has a suitable load cell mechanism, not illustrated, operatively associated therewith so as to in fact measure the extent of the load impressed upon each one of the anchor assemblies 28. Subsequently, the hydraulic pump 14 is cyclically operated so as to cause each one of the cracks 22 to be OPENED and CLOSED, by means of a predetermined amount, such as, for example, 0.012 inches (0.012") for one thousand (1000) cycles over the course of a predetermined period of time, such as, for example, three or four hours, during which time each one of the anchor assemblies 28 is effectively required to exhibit sufficient pull-out resistance so as not to be permitted to move upwardly within, or relative to, the concrete block 10 by means of a distance of more than 0.120 inches (0.120") or else the particular anchor assembly 28 will be considered to be a failure and therefore unacceptable for its intended usage. In connection with the monitoring of the movements of each one of the anchor assemblies 28, a second linearly variable displacement transformer (LVDT) 32, which may be operatively connected to the spring-loaded or hydraulic pump load assembly or bracket 30, may be employed to measure the distance that each one of the anchor assemblies 28 may move within the concrete block 10. It is to be appreciated, for example, that the cyclic testing of the anchor assemblies 28 within the concrete block 10, wherein the cracked regions 22 of the concrete block 10 are cyclically OPENED and CLOSED during the one thousand (1000) times or cycles, is designed to simulate, for example, environmental conditions wherein, for example, concrete substructures or substrates may expand and contract due to variances in ambient temperature conditions.

While it is noted that the aforenoted U.S. Pat. Nos. 5,911,550, 4,929,134, 4,904,135, 4,720,224, 1,115,205, and 1,000,715, which respectively issued to Popp et al., Bergner, Barthomeuf et al., Peterken, Johnson, and Caywood, are directed toward and disclose various anchoring assemblies for use within concrete or similar boreholes, it is additionally noted that none of the disclosed anchoring assemblies are directed toward an anchoring assembly which is specifically structured so as to assuredly satisfy or meet the requirements of the aforenoted cracked concrete testing procedures in order to ensure that not only will each anchoring assembly not exhibit failure and will in fact desirably exhibit high pull-out resistance and long service lives, but in addition, that the structural components, which have been secured to the concrete substrates or substructures by means of such anchoring assemblies, will be solidly and reliably affixed or secured to the underlying concrete substrate or substructure foundations. A need therefore exists in the art for a new and improved anchoring assembly which is specifically structured so as to assuredly satisfy or meet the requirements of the aforenoted cracked concrete testing procedures in order to ensure that not only will such anchoring assemblies not exhibit failure and will in fact desirably exhibit high pull-out resistance and long service lives, but in addition, that the structural components, which have been secured to the concrete substrates or substructures by means of such anchoring assemblies, will be solidly and reliably affixed or secured to the underlying concrete substrates or substructures.

SUMMARY OF THE INVENTION

The foregoing and other objectives are achieved in accordance with the teachings and principles of the present invention through the provision of a new and improved wedge type anchoring assembly which comprises an axially oriented anchor bolt and an annularly threaded or grooved expansion sleeve or clip annularly disposed around the axially oriented anchor bolt. The annularly threaded or grooved expansion sleeve or clip has a continuous array of annularly oriented grooves, threads, or teeth, comprising a predetermined number of grooves, threads, or teeth, which are disposed about the forward end external peripheral surface portion of the expansion sleeve or clip so as not to extend throughout the entire axial length of the expansion sleeve or clip. In addition, the annularly threaded or grooved expansion sleeve or clip is fabricated from a metal sheet or plate which is formed into the annularly grooved expansion sleeve or clip so as to have a substantially C-shaped cross-sectional configuration that enables the annularly grooved expansion sleeve or clip to be expanded by effectively being opened as the axially oriented anchor bolt is pulled therethrough.

It is also noted that each one of the annular teeth, threads, or grooves of the expansion sleeve or clip has a predetermined depth dimension, as measured between the root and crest portions thereof, which is larger than the distance that the cracked regions of the concrete block are opened during the cracked concrete testing technique or procedures so as to ensure the fact that the grooves, threads, or teeth of the expansion sleeve or clip effectively remain embedded within the side wall portions of the borehole formed within the concrete block. In addition, the internal peripheral surface portion of the annularly grooved expansion sleeve or clip, within the leading end portion thereof, and the external peripheral surface of the axially oriented anchor bolt, within the leading end portion thereof, have predetermined inclined slopes. All of these various features characteristic of the new and improved expansion sleeve or clip of the present invention effectively combine and contribute to the achievement of a maximum interference area (M.I.A.) or maximum interference volume (M.I.V.) as developed between the axially oriented anchor bolt and the annularly grooved expansion sleeve or clip, so as to, in turn, be developed between the annularly grooved expansion sleeve or clip and the internal peripheral side wall portions of the borehole formed within the concrete substrate or substructure so as to force the annularly grooved expansion clip or sleeve into its solidly affixed anchored disposition within a concrete borehole, to be formed within a concrete substrate or substructure, whereby the expansion sleeve or clip component will exhibit enhanced pull-out resistance properties.

BRIEF DESCRIPTION OF THE DRAWINGS

Various other features and attendant advantages of the present invention will be more fully appreciated from the following detailed description when considered in connection with the accompanying drawings in which like reference characters designate like or corresponding parts throughout the several views, and wherein:

FIG. 8a is a side elevational view, similar to that of FIG. 5, showing, however, a second embodiment of a sheet or plate from which the new and improved expansion sleeve component, of the new and improved anchor bolt and expansion sleeve assembly as has been illustrated within FIG. 3, can be fabricated by rolling or forming the sheet or plate in such manner that the finished expansion sleeve component has a substantially tubular configuration wherein the opposite side edge portions of the sheet or plate will be mated together along a longitudinally or axially oriented seam portion, and wherein the plurality of circumferentially spaced, triangularly configured barbs are angularly offset with respect to the longitudinal axis of the sheet or plate from which the new and improved expansion sleeve component is to be fabricated;

DETAILED DESCRIPTION OF THE PREFERRED EMBODIMENT

Figure 1:
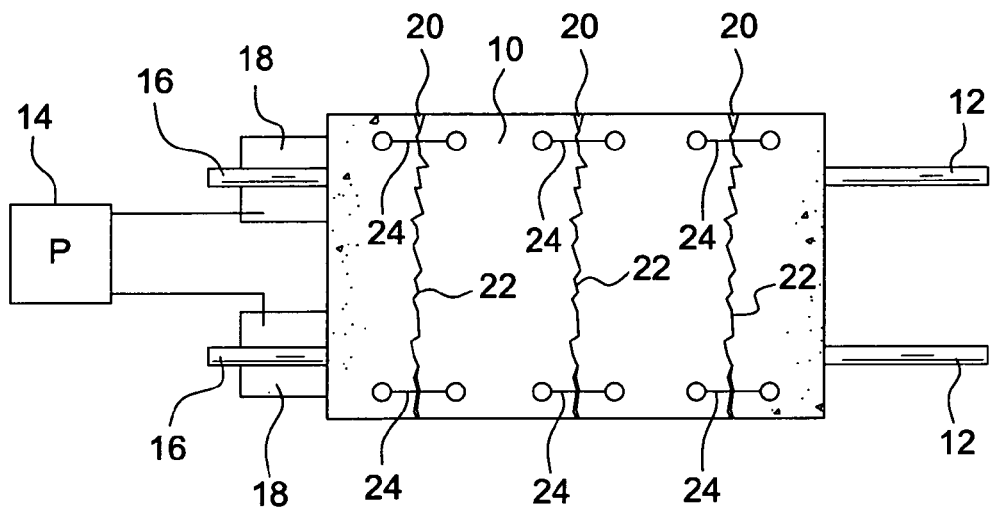
FIG. 1 is a schematic view of a concrete block having various structural components operatively connected thereto so as to permit the concrete block to undergo cracked concrete testing.
Figure 2:
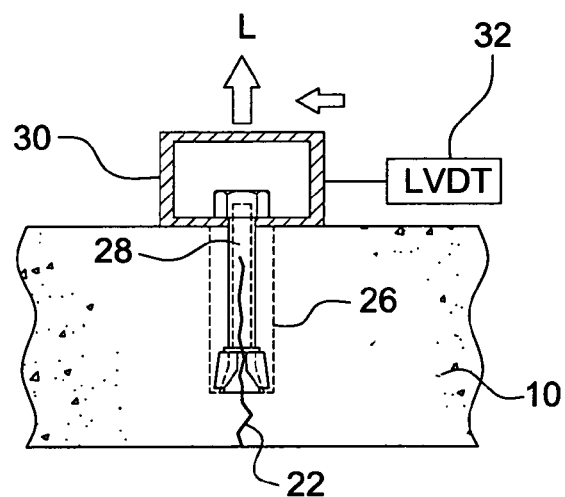
FIG. 2 is a schematic view of a portion of the concrete block, as illustrated within FIG. 1, wherein an anchor bolt and expansion sleeve assembly has been inserted into one of the boreholes formed within one of the cracked concrete regions so as to be ready for performance of the cracked concrete testing procedures.
Figure 3:
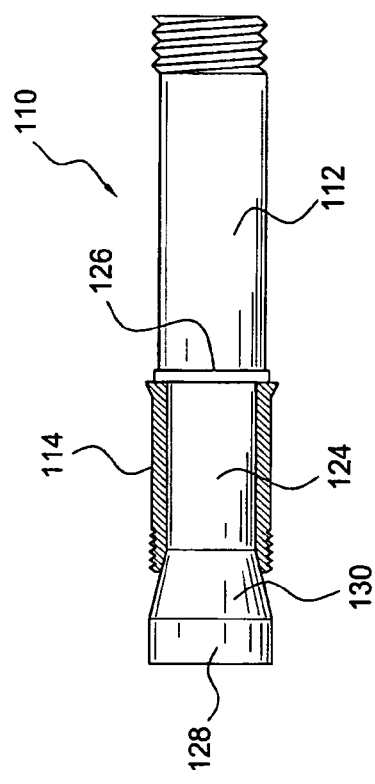
FIG. 3 is a side elevational view of a new and improved anchor bolt and expansion sleeve assembly which has been constructed in accordance with the principles and teachings of the present invention and which discloses the cooperative parts thereof.
Figure 4:
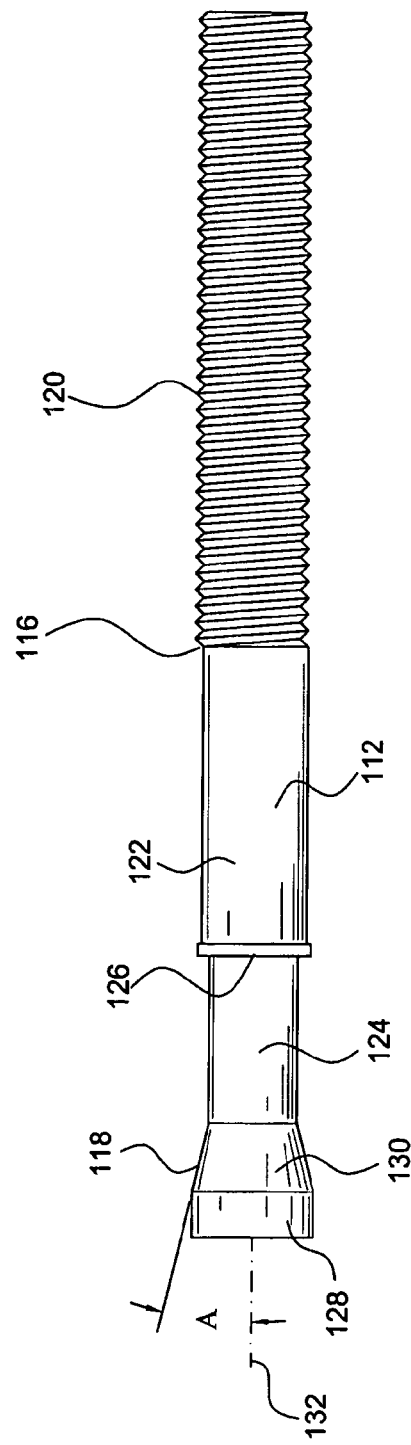
FIG. 4 is a side elevational view of the anchor bolt component, of the new and improved anchor bolt and expansion sleeve assembly as has been illustrated within FIG. 3, illustrating in detail the various structural features characteristic of the anchor bolt component of the new and improved anchor bolt and expansion sleeve assembly of the present invention.

Referring now to the drawings, and more particularly to FIG. 3 thereof, a new and improved anchor bolt and expansion sleeve assembly, which has been constructed in accordance with the principles and teachings of the present invention, and which is disclosed and generally indicated by the reference character 110, is seen to comprise an anchor bolt or threaded stud component 112 and an expansion sleeve component 114. More particularly, and as can be appreciated with reference being additionally made to FIG. 4, the anchor bolt or threaded stud component 112 is seen to comprise a shank portion 116 and a head portion 118. The rearward half of the shank portion 116 of the anchor bolt component 112 is externally threaded as at 120 so as to serve as a load-bearing or load-application member in a well-known manner, while the forward half of the shank portion 116 of the anchor bolt component 112 is non-threaded and comprises a stepped configuration comprising a relatively large-diameter rearwardly disposed section 122 and a relatively small-diameter forwardly disposed section 124. An annular flange member 126 is provided at the juncture of the relatively large-diameter rearwardly disposed section 122 and the relatively small-diameter forwardly disposed section 124 so as to effectively define an annular shoulder portion against or upon which the rear end portion of the expansion sleeve component 114 is adapted to be seated, prior to the expanded installation of the expansion sleeve component 114 within the borehole of a concrete substrate or substructure, as is illustrated within FIG. 3 and as will become more apparent hereinafter. Still further, it is seen that the head portion 118 of the anchor bolt component comprises a cylindrically configured forwardmost section 128, and a frusto-conically configured wedge-type section 130 that is interposed between, and integrally connects together, the cylindrically configured forwardmost section 128 of the head portion 118 and the relatively small-diameter forwardly disposed section 124 of the shank portion 116. It is lastly noted that the external annular or peripheral surface portion of the frusto-conically configured wedge-type section 130 of the head portion 118 of the anchor bolt component 112 is substantially smooth, continuous, and planar, and has an angular inclination with respect to the longitudinal axis 132 of the anchor bolt component 112, as denoted by means of the arrow A, of approximately 10°, the purpose of which will be discussed more fully hereinafter, although it is to be noted still further that this particular angle is for use upon, or in connection with, a one-half inch (0.500") diameter anchor, whereby other angled surfaces may be used in connection with otherwise dimensioned anchors.

With reference now being made to FIGS. 5-8, it is seen that the expansion sleeve component 114 is adapted to be fabricated from a metal sheet or plate having a thickness dimension of approximately 0.058 inches (0.058"), wherein, again, such dimensions are for use upon, or in connection with, a one-half inch (0.500") diameter anchor, however, other expansion sleeve components, having other thickness dimensions, may be used in connection with otherwise dimensioned anchors. The expansion sleeve component 114 may be fabricated, for example, from a suitable low-carbon steel with a zinc plating. This fabrication of the expansion sleeve component 114, from the metal material having the aforenoted thickness dimension, permits the expansion sleeve component 114 to be rolled into an annular or tubular structure, under the influence of forces schematically illustrated by means of the arrows F,F as shown, for example, within FIG. 6, whereby the oppositely disposed side edge portions 134,136 of the expansion sleeve component 114 will be brought toward and into near proximity or substantial contact with each other so as to create a longitudinally or axially oriented seam portion. Alternatively, the expansion bolt may be fabricated from a suitable carbon steel composition which is, in turn, plated with a zinc-tin plating. The zinc-tin plating permits the expansion sleeve component 114 to exhibit a desired amount of friction with respect to the borehole of the concrete substrate or substructure and yet permits the anchor bolt or threaded stud component 112 to move in a desirably controlled manner with respect to the expansion sleeve component 114.

The formation of the expansion sleeve component 114 as the tubular structure having, in effect, a substantially C-shaped cross-sectional configuration, as opposed to a solid tubular or annular expansion sleeve component, is a desirable feature characteristic of the new and improved expansion sleeve component 114 of the present invention because such structure permits the expansion sleeve component 114 to open immediately and undergo radially outward expansion when the anchor bolt component 112 of the new and improved anchor bolt and expansion sleeve assembly 110 is moved relative to the expansion sleeve component 114. This relative movement of the anchor bolt component 112 relative to the expansion sleeve component 114 causes the head portion 118 of the anchor bolt component 112 to forcefully expand the expansion sleeve component 114 into interference contact with, and the crushing of, the internal peripheral surface portion of the concrete wall defining the borehole within the concrete substrate or substructure, as will be discussed and illustrated in more detail hereinafter. This is to be contrasted with a typical solid tubular or annular expansion sleeve component which must initially undergo plastic deformation, by means of the anchor bolt component, prior to achieving interference contact with, and the crushing of, the internal peripheral surface portion of the concrete wall defining the borehole within the concrete substrate or substructure.

Figure 5:
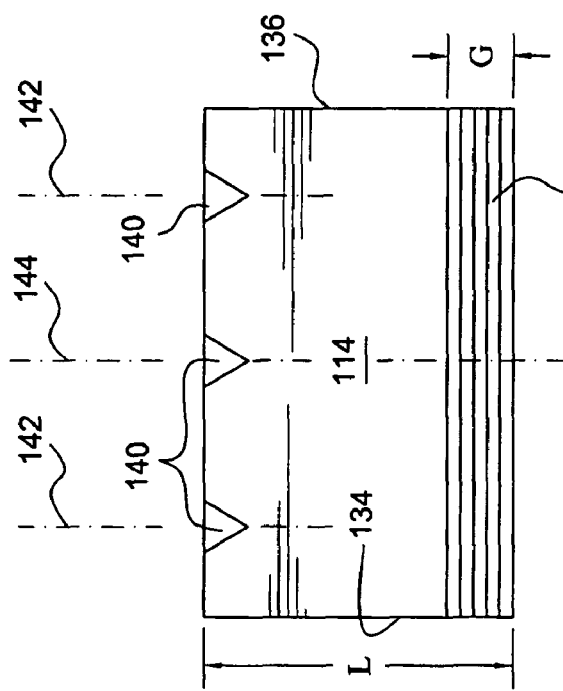
FIG. 5 is a side elevational view of a sheet or plate from which the new and improved expansion sleeve component, of the new and improved anchor bolt and expansion sleeve assembly as has been illustrated within FIG. 3, can be fabricated by rolling or forming the sheet or plate in such manner that the finished expansion sleeve component has a substantially tubular configuration wherein the opposite side edge portions of the sheet or plate will be mated together along a longitudinally or axially oriented seam portion.
Figures 7, 8:
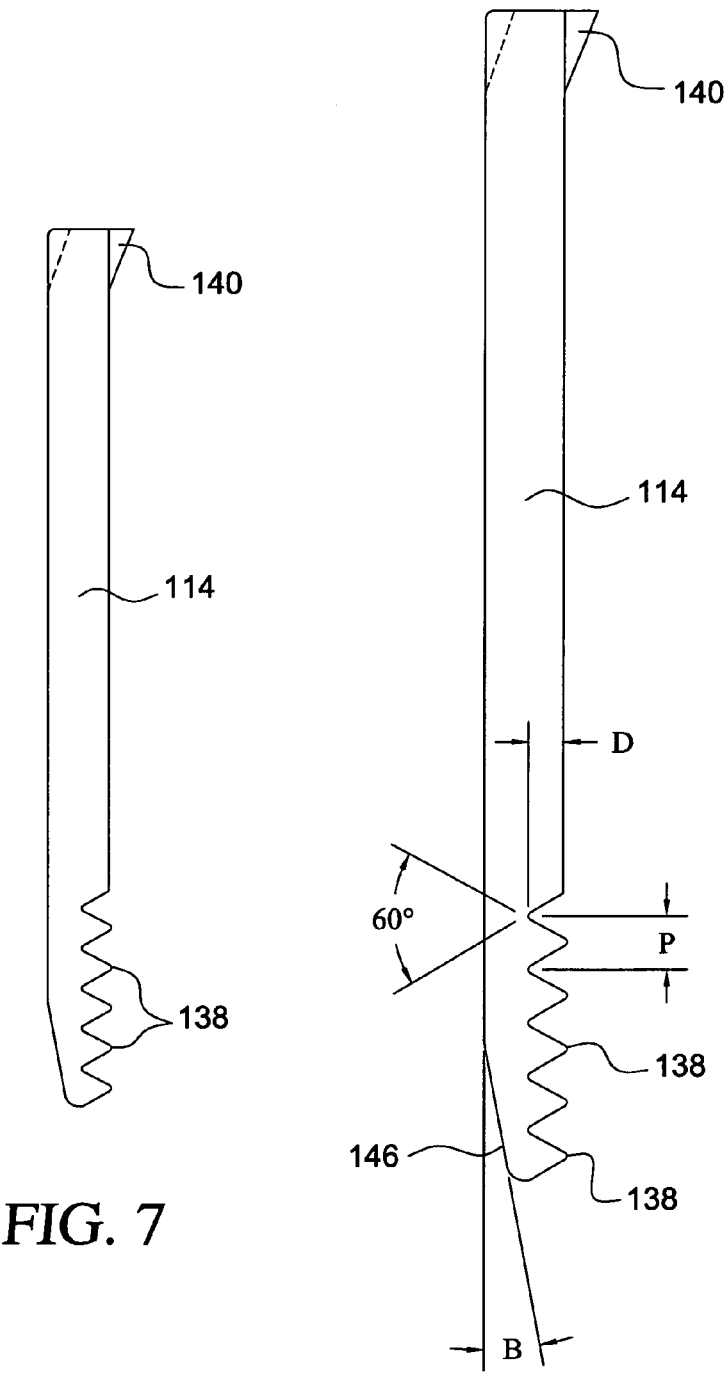
FIG. 7 is an end elevational view of the sheet or plate, as illustrated within FIG. 5, before the sheet or plate is rolled or formed into the new and improved expansion sleeve component of the new and improved anchor bolt and expansion sleeve assembly, showing the various structural features thereof.
FIG. 8 is an enlarged, end elevational view of the sheet or plate, as illustrated within FIG. 7, before the sheet or plate is rolled or formed into the new and improved expansion sleeve component of the new and improved anchor bolt and expansion sleeve assembly, more clearly showing the details of the various structural features thereof.

Continuing further, it is also to be appreciated from FIG. 5 that the expansion sleeve component 114 has a longitudinal or axial length dimension L which may comprise, for example, 0.866 inches (0.866"), again, when being used upon or in connection with a one-half inch (0.500") diameter anchor, and that a plurality of annular grooves, teeth, or threads 138, as can also be clearly seen and appreciated from FIGS. 7 and 8, are provided upon the forwardmost external surface portion of the expansion sleeve component 114. More particularly, it is seen that the plurality of annular teeth, grooves, or threads 138 comprises, for example, five, contiguously disposed annularly oriented grooves, teeth, or threads 138, and that the five, contiguously disposed, annularly oriented grooves, teeth, or threads 138 are only provided upon the forwardmost one-quarter portion of the expansion sleeve component 114 such that the five, contiguously disposed, annularly oriented grooves, teeth, or threads 138 extend over a longitudinal or axial extent portion of approximately 0.200 inches (0.200"). The provision of the five, contiguously disposed, annularly oriented grooves, teeth, or threads 138, only upon the forwardmost one-quarter portion of the expansion sleeve component 114, as opposed to having such annularly oriented grooves, teeth, or threads formed upon the expansion sleeve component 114 throughout the entire longitudinal or axial length thereof, also comprises another desirable structural feature characteristic of the new and improved annular expansion sleeve component 114 in that, as will be discussed and illustrated more fully in detail hereinafter, such structure enables the new and improved annular expansion sleeve component 114 to achieve a predetermined maximum interference area with, and to effectively crush, the internal peripheral surface portion of the concrete wall defining the borehole formed within the concrete substrate or substructure.

Figure 6:
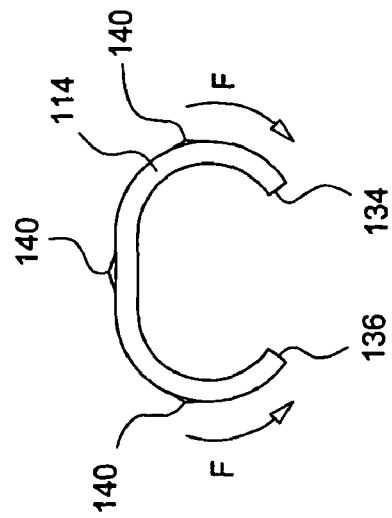
FIG. 6 is a top plan view of the sheet or plate, as illustrated within FIG. 5, wherein the sheet or plate is being rolled or formed in such a manner that the opposite side edge portions of the sheet or plate will be mated together along the longitudinally or axially oriented seam portion whereby the resulting, new and improved expansion sleeve component, of the new and improved anchor bolt and expansion sleeve assembly, will have its substantially tubular configuration.

As can also be seen from FIGS. 5-7, a plurality of circumferentially spaced, triangularly configured barbs 140 are provided upon the rearwardmost external surface portion of the expansion sleeve component 114. In this manner, as the anchor bolt and expansion sleeve assembly 110 is inserted into the borehole defined within the concrete substrate or substructure, the plurality of barbs 140 will effectively bite into, or become embedded within, the internal peripheral surface portion of the concrete wall defining the borehole within the concrete substrate or substructure so as to thereby prevent rotation and reverse movement of the expansion sleeve component 114 with respect to the borehole defined within the concrete substrate or substructure. Alternatively, as can be appreciated from FIG. 8a, a second embodiment of a sheet or plate, from which a new and improved expansion sleeve component 214, of the new and improved anchor bolt and expansion sleeve assembly as has been illustrated within FIG. 3, can be fabricated by rolling or forming the sheet or plate in such manner that the finished expansion sleeve component has a substantially tubular configuration wherein the opposite side edge portions of the sheet or plate will be mated together along a longitudinally or axially oriented seam portion, is disclosed. It is to be appreciated that the second embodiment expansion sleeve component 214 is substantially the same as the first embodiment expansion sleeve component 114 as disclosed within, for example, FIG. 5, except as will be described shortly hereinafter, and accordingly, those component parts of the second embodiment expansion sleeve component 214, which correspond to the component parts of the first embodiment expansion sleeve component 114, will be designated by corresponding reference characters except that they will be within the 200 series.

More particularly, it is to be appreciated that the only significant difference between the second embodiment expansion sleeve component 214 and the first embodiment expansion sleeve component 114 resides in the orientation or disposition of the barbs 140,240 upon the respective sheet or plate from which the expansion sleeve components 114,214 are to be fabricated. More specifically, while the plurality of circumferentially spaced, triangularly configured barbs 140 of the first embodiment expansion sleeve component 114 have their primary longitudinal axes 142 substantially aligned with or disposed parallel to the longitudinal axis 144 of the sheet or plate from which the expansion sleeve component 114 is to be fabricated, the plurality of circumferentially spaced, triangularly configured barbs 240 of the second embodiment expansion sleeve component 214 have their axes 242 angularly offset or disposed at a predetermined angle A, such as, for example, 20°, with respect to the longitudinal axis 244 of the sheet or plate from which the expansion sleeve component 214 is to be fabricated.

The reason for this is that as the anchor bolt and expansion sleeve assembly is inserted into the borehole defined within the concrete substrate or substructure, the plurality of angularly offset barbs 240 will not only effectively bite into, or become embedded within, the internal peripheral surface portion of the concrete wall defining the borehole within the concrete substrate or substructure so as to thereby prevent rotation and reverse movement of the expansion sleeve component 214 with respect to the borehole defined within the concrete substrate or substructure, as was the case with the plurality of barbs 140, but in addition, since such angularly offset barbs 240 will in effect form grooves within the borehole of the concrete substrate or substructure which will be disposed at an angle to the longitudinal axis of the borehole, the tendency of the expansion sleeve component 214 to effectively back itself, and the anchor bolt and expansion sleeve assembly, out of the borehole, is significantly negated because the expansion sleeve component 214 would have to effectively undergo reverse angular rotation which is not normally going to occur under natural forces attendant an embedded anchor bolt and expansion sleeve assembly within a borehole of a concrete substrate or substructure. Accordingly, the anchor bolt and expansion sleeve assembly will exhibit enhanced pull-out resistance characteristics.

As can also be appreciated with reference being additionally being made to FIG. 8, it is seen that each one of the plurality of annularly oriented grooves, teeth, or threads 138 have forwardly and rearwardly disposed flank surface portions that are disposed at an angle of approximately 60° with respect to each other, and that the pitch P of the grooves, teeth, or threads 138, as defined between successive ones of the plurality of grooves, teeth, or threads, as measured, for example, between successive root portions of the plurality of grooves, teeth, or threads 138, is approximately 0.039 inches (0.039") in view of the fact that the grooves, teeth, or threads 138 have been machined into the expansion sleeve component 114 in accordance with twenty-eight (28) threads per inch thread formation techniques. While twenty-eight (28) threads per inch is preferred, threads within the range of twenty (20) to thirty-two (32) may be employed. In addition, it is to be further appreciated that, in accordance with another desirable feature which is characteristic of the present invention, each one of the annularly oriented teeth, grooves, or threads 138 has a radial depth dimension D, as measured between the root portion of the particular tooth, groove, or thread, and the crest portion of the particular groove, tooth, or thread, that is within the range of 0.015-0.050 inches (0.015-0.050"). The significance of such depth dimensions is that when, for example, the new and improved anchor bolt and expansion sleeve assembly 110 is inserted within a borehole defined within a concrete substrate or concrete substructure, and when the aforenoted cracked concrete testing procedures are subsequently conducted in connection with the new and improved anchor bolt and expansion sleeve assembly 110 wherein, for example, as has been noted hereinbefore, the cracked concrete is cycled between its OPEN and CLOSED states, comprising, for example, the predetermined amount or distance of 0.012 inches (0.012"), the annularly oriented grooves, teeth, or threads 138 will in fact remain embedded within the internal peripheral side wall portions of the boreholes which have been previously formed within the concrete substrate or substructure. As has also been noted hereinbefore, such testing procedures have been designed to simulate real-world conditions so as to ensure that anchor assemblies used within on-site locations will exhibit satisfactory performance characteristics and will not exhibit or experience failure.

Alternatively, it is to be noted that different ones of the annularly oriented grooves, teeth, or threads 138 may have different radial depth dimensions D, as measured between the root portion of the particular tooth, groove, or thread, and the crest portion of the particular groove, tooth, or thread, however, the radial depth dimension would still be sufficiently large so as to ensure the fact that the teeth, grooves, or threads not only remain embedded within the internal side wall portions of the concrete block 10 during the cracked concrete testing procedures, but just as importantly, that the teeth, grooves, or threads would remain embedded within the internal side wall portions of the concrete substrate or substructure during real variable environmental conditions during which the concrete substrate or substructure would undergo expansion and contraction. It is also noted that the radially outward extents or crest portions of the plurality of annularly oriented grooves, threads, or teeth 138 do not extend beyond the outside diametrical extent of the body portion of the new and improved expansion sleeve component 114. This comprises another desirable feature characteristic of the new and improved expansion sleeve component 114 in view of the fact that when the new and improved anchor bolt and expansion sleeve assembly 110 is inserted into the borehole defined within the concrete substrate or substructure, the radially outward extents or crest portions of the plurality of annularly oriented grooves, teeth, or threads 138 will not adversely, deleteriously, and undesirably gouge or abrade the internal side wall surface portions of the borehole defined within the concrete substrate or substructure.

Continuing further, it is also seen that the internal peripheral surface portion of the new and improved expansion sleeve component 114 is inclined radially outwardly at the forwardmost end portion thereof, as considered in the longitudinal or axial direction extending from the rearward or upstream end portion of the expansion sleeve component 114 to the forward or downstream end portion of the expansion sleeve component 114, as illustrated at 146. More particularly, it is noted that the inclined internal peripheral surface portion 146 of the expansion sleeve component 114 is disposed at an angular inclination with respect to a line or plane parallel to the longitudinal axis of the expansion sleeve component 114, as denoted by means of the arrow B, of approximately 10° which is, as will be recalled, substantially the same angular inclination of the external peripheral surface portion of the frusto-conically configured wedge-type section 130 of the head portion 118 of the anchor bolt component 112 with respect to the longitudinal axis 132 of the anchor bolt component 112. Accordingly, the inclined internal peripheral surface portion 146 of the expansion sleeve component 114 and the external peripheral surface portion of the frusto-conically configured wedge-type section 130 of the head portion 118 of the anchor bolt component 112 together define mating surface portions which have substantially or approximately matching inclinations.

In addition, as was the case with the external peripheral surface portion of the frusto-conically configured wedge-type section 130 of the head portion 118 of the anchor bolt component 112, the internal peripheral surface portion 146 of the expansion sleeve component 114 is substantially smooth, continuous, and planar so that, together, the external peripheral surface portion of the frusto-conically configured wedge-type section 130 of the head portion 118 of the anchor bolt component 112, and the internal peripheral surface portion 146 of the expansion sleeve component 114, define or comprise the largest possible common conical surface area throughout their longitudinal and angular extents. The significance of the foregoing, which will be appreciated even more fully hereinafter, resides in the fact that when the expansion sleeve component 114 and the anchor bolt component 112 are assembled together so as to form the new and improved anchor bolt and expansion sleeve assembly 110 as disclosed within FIG. 3, and when the anchor bolt component 112 is subsequently moved axially with respect to the expansion sleeve component 114 so as to cause the radially outward expansion of the expansion sleeve component 114 with respect to the internal side wall portions of the borehole within which the new and improved anchor bolt and expansion sleeve assembly 110 is disposed, the external peripheral surface portion of the frusto-conically configured wedge-type section 130 of the head portion 118 of the anchor bolt component 112 will immediately cause the radially outward expansion of the expansion sleeve component 114 with respect to the internal side wall portions of the borehole within which the new and improved anchor bolt and expansion sleeve assembly 110 is disposed.

It is to be appreciated that if the angular inclination B of the internal peripheral surface portion 146 of the expansion sleeve component 114 was significantly less than the angular inclination A of the external peripheral surface portion of the frusto-conically configured wedge-type section 130 of the head portion 118 of the anchor bolt component 112 so as to be substantially mismatched, then it may be somewhat difficult to initially properly seat the expansion sleeve component 114 upon the anchor bolt component 112 as illustrated within FIG. 3, or, in other words, the external peripheral surface portion of the frusto-conically configured wedge-type section 130 of the head portion 118 of the anchor bolt component 112 would have to initially cause some radially outward deformation of the leading end portion 146 of the expansion sleeve component 114. Alternatively, if the angular inclination B of the internal peripheral surface portion 146 of the expansion sleeve component 114 was significantly greater than the angular inclination A of the external peripheral surface portion of the frusto-conically configured wedge-type section 130 of the head portion 118 of the anchor bolt component 112, then the anchor bolt component 112 would have to undergo substantially more axial displacement in the rearward direction, with respect to the expansion sleeve component 114, before, for example, engaged contact, between the external peripheral surface portion of the frusto-conically configured wedge-type section 130 of the head portion 118 of the anchor bolt component 112 and the internal peripheral surface portion 146 of the expansion sleeve component 114, could be established.

With reference lastly being made to FIGS. 9a-9k and FIG. 10, the operational attributes and advantages that are characteristic, or exhibited by means, of the new and improved anchor bolt and expansion sleeve assembly 110 of the present invention will now be disclosed and described as a function of the installation of the new and improved anchor bolt and expansion sleeve assembly 110 within a borehole defined or formed within a concrete substrate or substructure. More particularly, FIGS. 9a-9k schematically disclose or illustrate the new and improved anchor bolt and expansion sleeve assembly 110 as the anchor bolt component 112 of the new and improved anchor bolt and expansion sleeve assembly 110 is axially moved, in increments of tenths of an inch, in a sequential manner with respect to the expansion sleeve component 114 of the new and improved anchor bolt and expansion sleeve assembly 110, while FIG. 10 graphically illustrates the total interference area generated between a section of the anchor bolt component 112, of the new and improved anchor bolt and expansion sleeve assembly 110, and the expansion sleeve component 114 of the new and improved anchor bolt and expansion sleeve assembly 110, and correspondingly, or in turn, the total interference area that will be generated between the expansion sleeve component 114 of the new and improved anchor bolt and expansion sleeve assembly 110 and the internal peripheral side walls of the borehole defined or formed within the concrete substrate or substructure, as a function of the axial displacement of the anchor bolt component 112 of the new and improved anchor bolt and expansion sleeve assembly 110 with respect to the expansion sleeve component 114 of the new and improved anchor bolt and expansion sleeve assembly 110.

More particularly, still further, it can be appreciated that when the installation process is initiated, the expansion sleeve component 114 of the new and improved anchor bolt and expansion sleeve assembly 110 will be disposed upon the anchor bolt component 112 of the new and improved anchor bolt and expansion sleeve assembly 110 such that the rearward or upstream end portion of the expansion sleeve component 114 will be seated upon, or disposed in abutment with, the annular collar or flanged shoulder member 126 of the new and improved anchor bolt component 112. At this point in time, the inclined or sloped internal peripheral surface portion 146 of the expansion sleeve component 114 will be seated upon, or disposed in substantial surface contact with, the similarly inclined or sloped external peripheral surface portion 130 of the anchor bolt component 112. Accordingly, no interference area forces are as yet effectively generated. However, as the anchor bolt component 112 begins to be moved axially rearwardly with respect to the expansion sleeve component 114, the larger diameter forwardly disposed or downstream sections of the inclined or sloped external peripheral surface portion 130 of the anchor bolt component 112 will begin to, and will progressively, engage the inclined or sloped internal peripheral surface portion 146 of the expansion sleeve component 114 so as to initially and progressively cause the C-shaped expansion sleeve component 114 to be OPENED and expanded radially outwardly. At this point in time, several unique and novel features, characteristic of the new and improved anchor bolt and expansion sleeve assembly 110, are to be appreciated.

Figure 9A:
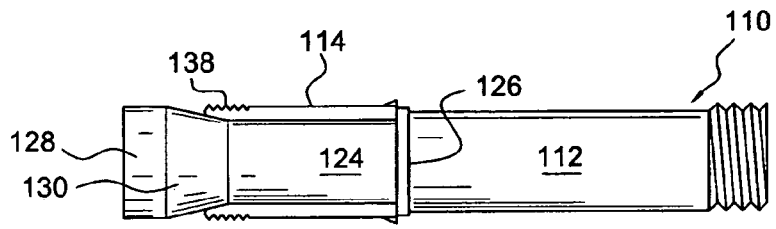
FIGS. 9a-9k are schematic views showing the progressive incremental movement of the anchor bolt component, of the new and improved anchor bolt and expansion sleeve assembly of the present invention as illustrated within FIG. 3, relative to the expansion sleeve component of the new and improved anchor bolt and expansion sleeve assembly, whereby as the anchor bolt component is incrementally moved with respect to the new and improved expansion sleeve component, different amounts of interference area, as developed between the anchor bolt component and the new and improved expansion sleeve component, are achieved.
Figure 9B:
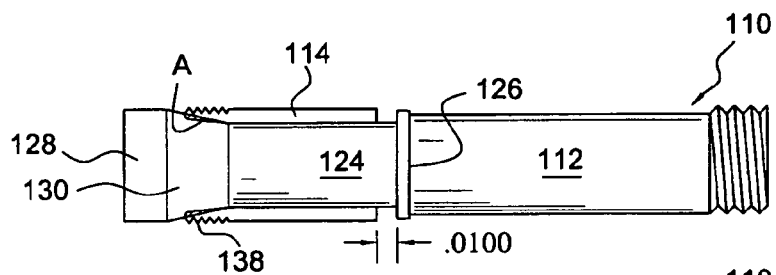
Figure 9C:
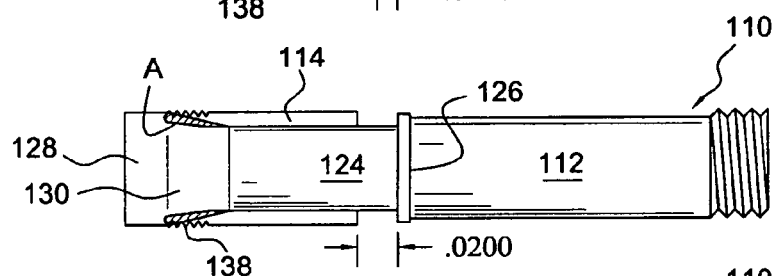
Figure 9D:
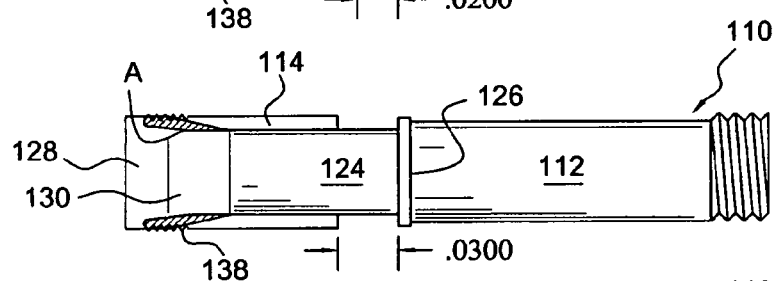
Figure 9E:
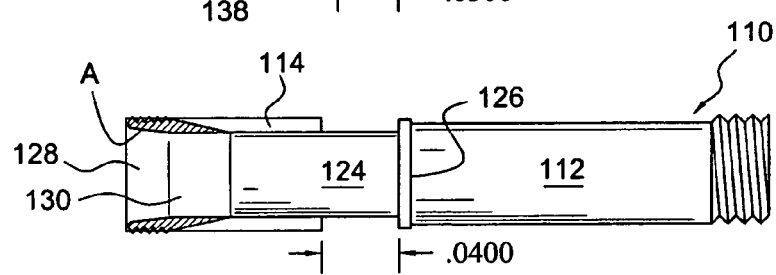
Figure 9F:
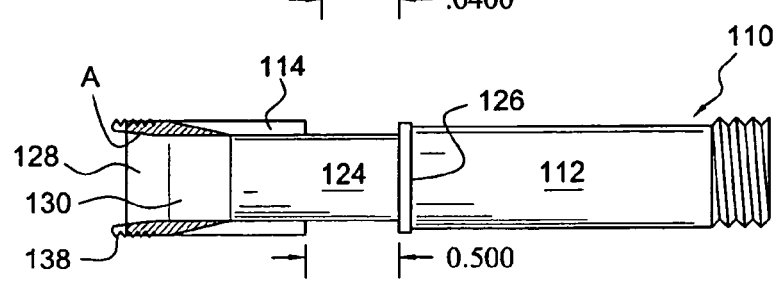
Figure 9G:
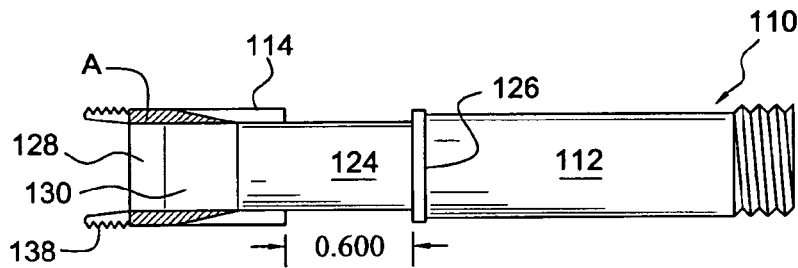
Figure 9H:
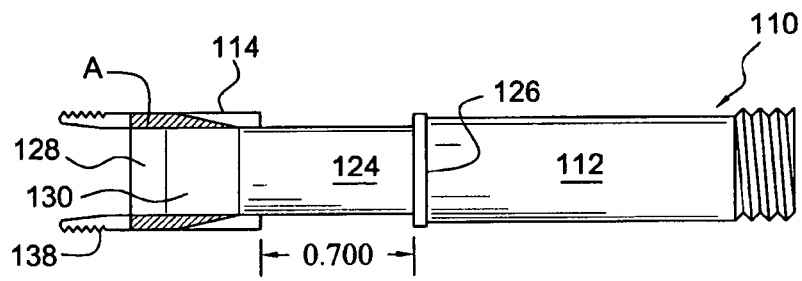

Firstly, it is to be noted and appreciated that as the anchor bolt component 112 progressively engages the inclined or sloped internal peripheral surface portion 146 of the expansion sleeve component 114 during the incremental movements of the anchor bolt component 112, between its starting point, as disclosed within FIG. 9a, and the point at which the anchor bolt component 112 has been axially moved, relative to the expansion sleeve component 114 through means of the axial distance of, for example, 0.600 inches (0.600"), which would again be characteristic of a one-half inch (0.050") diameter anchor, both the larger diameter forwardly disposed or downstream sections of the inclined or sloped external peripheral surface portion of the frusto-conically configured wedge-type section 130 of the head portion 118 of the anchor bolt component 112, and the larger diameter forwardly disposed or downstream sections of the cylindrically configured forwardmost section 128 of the head portion 118 of the anchor bolt component 112, will cause progressively more axially located annular portions of the annularly grooved, threaded, or toothed portion 138 of the expansion sleeve component 114 to be expanded radially outwardly and into engagement with the internal peripheral side wall portions of the borehole defined within the concrete substrate or substructure. Accordingly, the total area interference, as taken along a single axially oriented plane, as generated between the anchor bolt component 112 of the new and improved anchor bolt and expansion sleeve assembly 110, and the expansion sleeve component 114 of the new and improved anchor bolt and expansion sleeve assembly 110, as well as between the expansion sleeve component 114 and the internal peripheral side wall portions of the borehole formed or defined within the concrete substrate or substructure will be constantly increased as schematically illustrated by means of the blackened areas A within FIGS. 9b-9k and as graphically illustrated within FIG. 10.

The reason for the aforenoted phenomena resides in the fact that as the larger diameter forwardly disposed or downstream sections of the inclined or sloped external peripheral surface portion of the frusto-conically configured wedge-type section 130 of the head portion 118 of the anchor bolt component 112, as well as the larger diameter forwardly disposed or downstream sections of the cylindrically configured forwardmost section 128 of the head portion 118 of the anchor bolt component 112 of the new and improved anchor bolt and expansion sleeve assembly 110, encounter and engage the forwardly disposed or downstream end portion of the expansion sleeve component 114, upon which the annularly grooved, threaded, or toothed portions 138 of the expansion sleeve component 114 are disposed, progressively more and more annular, axially located, radially oriented cross-sections of the annularly grooved, threaded, or toothed portions 138 of the expansion sleeve component 114 will be expanded radially outwardly and into engagement with the internal peripheral side wall portions of the borehole defined within the concrete substrate or substructure. This ever-increasing volumetric interference is effectively graphically illustrated within FIG. 10. More particularly, it is to be appreciated that FIG. 10 actually graphically illustrates the total interference area defined between those annularly grooved, threaded, or toothed portions 138 of the expansion sleeve component 114 and the internal side wall portions of the borehole defined within the concrete substrate or substructure, as taken along only one axially oriented plane. However, the total volumetric interference can of course be readily obtained or calculated from the entire three-dimensional 360° expanse of the expansion sleeve component 114 when considered with respect to the entire internal peripheral side wall portions of the borehole defined within the concrete substrate or substructure.

Figure 10:
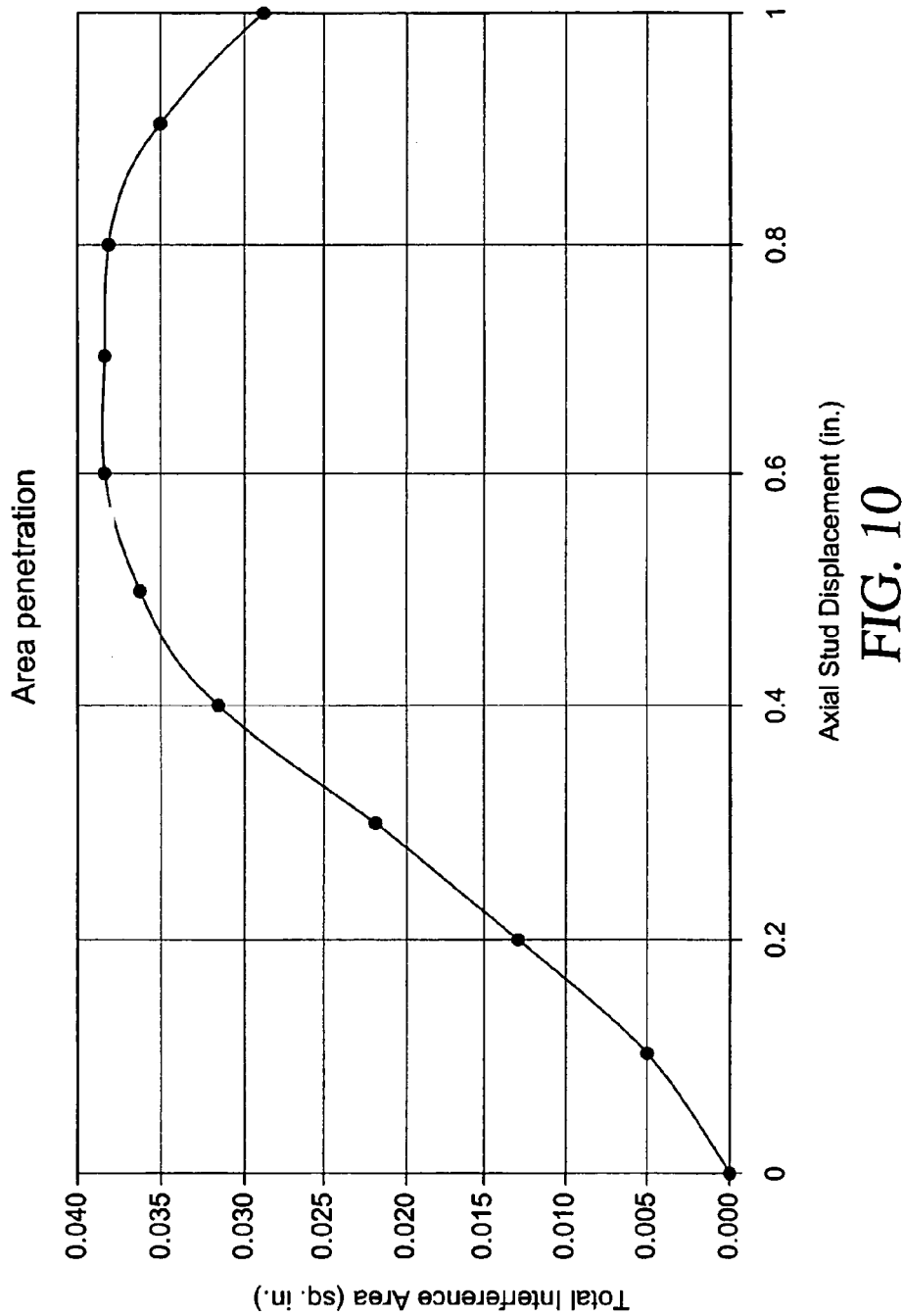
FIG. 10 is a graph illustrating the progressive interference area, that is developed between the anchor bolt component and the new and improved expansion sleeve component, and which will, in turn, be developed between the annularly grooved expansion sleeve or clip and the internal peripheral side wall portions of the borehole formed within the concrete substrate or substructure, as a function of the incremental displacement of the anchor bolt component with respect to the new and improved expansion sleeve component, as the anchor bolt component is progressively drawn through the new and improved expansion sleeve component in an incremental manner, as has been illustrated within FIGS. 9a-9k.

Continuing still further, it is secondly noted that as a result of providing the forwardly disposed or downstream end portion of the expansion sleeve component 114 with only the predetermined number of annularly grooved, threaded, or toothed portions 138, that is, for example, three to eight annularly grooved, toothed, or threaded portions 138, with five annularly grooved, toothed, or threaded portions 138 being preferred, the ever-increasing interference area or interference volume, as defined between the annularly grooved, threaded, or toothed portions 138 of the expansion sleeve component 114 and the internal peripheral side wall portions of the borehole defined within the concrete substrate or substructure, and as graphically illustrated in FIG. 10, has a predeterminedly desired slope whereby the maximum interference area (M.I.A.) or maximum interference volume (M.I.V.) is ultimately achieved when the anchor bolt component 112, of the new and improved anchor bolt and expansion sleeve assembly 110, has been axially moved approximately 0.600 inches (0.600") with respect to the expansion sleeve component 114 of the new and improved anchor bolt and expansion sleeve assembly 110. The reason for this is that when the anchor bolt component 112 has been axially moved approximately 0.600 inches (0.600") with respect to the expansion sleeve component 114, the larger diameter forwardly disposed or downstream sections of the inclined or sloped external peripheral surface portion of the frusto-conically configured wedge-type section 130 of the head portion 118 of the anchor bolt component 112, followed by the larger diameter forwardly disposed or downstream sections of the cylindrically configured forwardmost section 128 of the head portion 118 of the anchor bolt component 112 will now engage the rearward or upstream solid, non-grooved, non-threaded, non-toothed portions of the expansion sleeve component 114.

More particularly, it is to be appreciated that such solid, non-grooved, non-threaded, non-toothed portions of the new and improved expansion sleeve component 114 define a larger or greater area or volume of solid material comprising the expansion sleeve component 114 than the area or volume of solid material defined within the annularly grooved, threaded, or toothed regions 138 of the expansion sleeve component 114, and accordingly, a larger or greater area or volume of the internal peripheral side wall portions of the borehole, defined within the concrete substrate or substructure, will be engaged and effectively crushed by means of the expansion sleeve component 114. Therefore, the maximum interference area (M.I.A.), or the maximum interference volume (M.I.V.), as defined between the expansion sleeve component 114 and the internal peripheral side wall portions of the borehole defined within the concrete substructure or substrate, is able to be achieved.

Figure 9I:
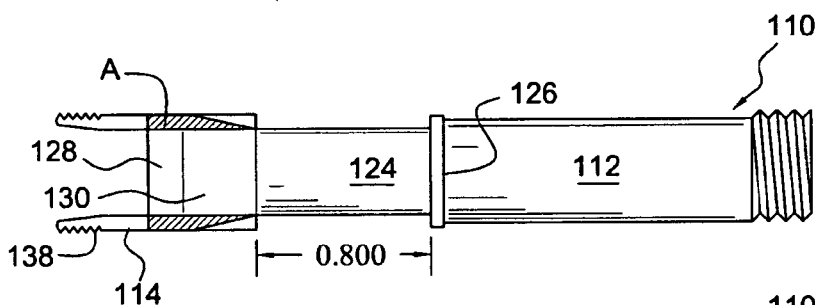
Figure 9J:
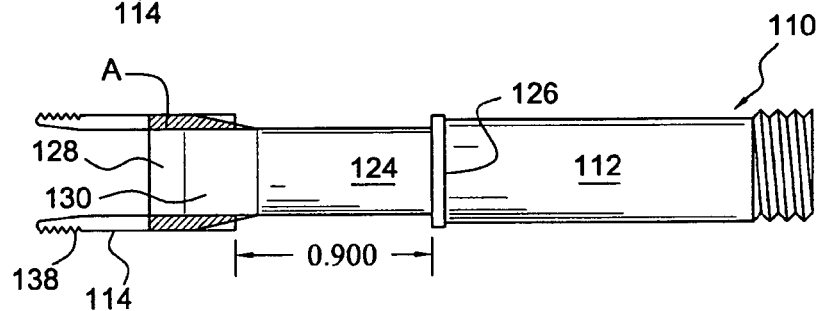
Figure 9K:
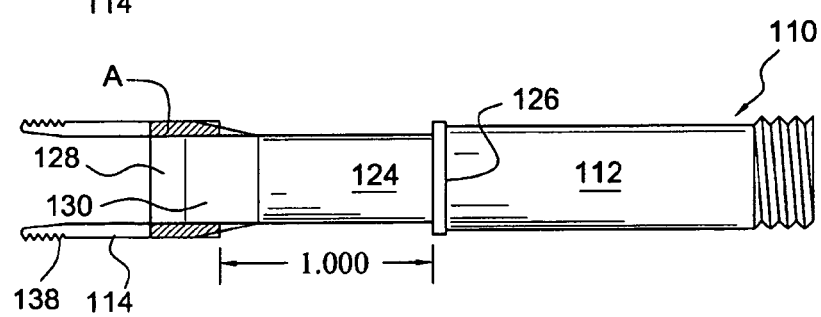

Continuing further, this maximum interference area (M.I.A.) and maximum interference volume (M.I.V.) continues until the anchor bolt component 112 has effectively been moved rearwardly with respect to the expansion sleeve component 114 through means of an axial distance of approximately eight-tenths of an inch (0.800") because at that point in time, as can be best appreciated from a comparison of FIGS. 9i and 9j, the rearward or upstream end portion of the frusto-conically configured wedge-type section 130 of the head portion 118 of the anchor bolt component 112 is just ready, and begins, to exit from the rearward or upstream end portion of the expansion sleeve component 114. Accordingly, the maximum amount of solid material, comprising the frusto-conically configured wedge-type section 130 of the head portion 118 of the anchor bolt component 112, and the larger diameter forwardly disposed or downstream sections of the cylindrically configured forwardmost section 128 of the head portion 118 of the anchor bolt component 112, which had previously been disposed in forceful, contact engagement with the solid portion of the expansion sleeve component 114 will no longer be so disposed. To the contrary, only a reduced amount of the solid material, comprising the frusto-conically configured wedge-type section 130 of the head portion 118 of the anchor bolt component 112, and the larger diameter forwardly disposed or downstream sections of the cylindrically configured forwardmost section 128 of the head portion 118 of the anchor bolt component 112, will now be disposed in forceful, contact engagement with the solid portion of the expansion sleeve component 114. In fact, the amount of solid material, comprising the frusto-conically configured wedge-type section 130 of the head portion 118 of the anchor bolt component 112, and the larger diameter forwardly disposed or downstream sections of the cylindrically configured forwardmost section 128 of the head portion 118 of the anchor bolt component 112, that will be disposed in forceful, contact engagement with the solid portion of the expansion sleeve component 114, will be progressively reduced as the anchor bolt component 112 continues to move axially rearwardly with respect to the expansion sleeve component 114 whereby the amount of interference area, or interference volume, is progressively reduced and tapers off as can be appreciated from FIGS. 9j,9k, and FIG. 10.

In connection with the aforenoted generation of the interference area and interference volume, as defined between the anchor bolt component 112 and the expansion sleeve component 114 of the new and improved anchor bolt and expansion sleeve assembly 110, as well as between the expansion sleeve component 114 and the internal peripheral side wall portions of the borehole defined within the concrete substrate or substructure, it is to be appreciated that if a significantly smaller number than, for example, three to eight, annular grooves, teeth, or threads 138, were used, that is, if only one or two annular threads, grooves, or teeth were used, then while the slope of the graphical plot would effectively be steeper than that as illustrated within FIG. 10, indicating, in effect, that the maximum interference area (M.I.A.) or maximum interference volume (M.I.V.) would effectively be achieved in a shorter amount of time, that is, as a result of a smaller axial stud displacement in view of the fact that the solid, non-grooved, non-threaded, or non-toothed portions of the expansion sleeve component 114 would effectively come into play and engage the internal peripheral side wall portions of the borehole, defined within the concrete substrate or substructure, sooner, the ability to actually embed a sufficient number of the annular teeth, grooves, or threads within the internal peripheral side wall portions of the borehole, defined within the concrete substrate or substructure, would not be sufficient in order to provide the necessary or requisite holding power or pull-out resistance required in connection with the cracked concrete testing procedures.

Alternatively, if a significantly larger number than, for example, three to eight annular grooves, teeth, or threads 138, were used, then the slope of the graphical plot would be shallower than that as illustrated within FIG. 10 thereby indicating, in effect, that it would effectively take longer to achieve the desired and maximum interference area (M.I.A.) or maximum interference volume (M.I.V.), whereby, again, the ability to provide the necessary or requisite holding power or pull-out resistance required in connection with the cracked concrete testing procedures might not be able to be achieved. More particularly, if this last scenario was carried to the extreme wherein the external surface portion of the expansion sleeve component 114 was entirely characterized by means of annular grooves, teeth, or threads, and was therefore entirely devoid of the aforenoted non-grooved, non-toothed, or non-threaded solid portions within the upstream end regions thereof, then the aforenoted crushed engagement of the internal peripheral side wall portions of the borehole, defined within the concrete substrate or substructure, would never be achieved so that, in turn, the maximum interference area (M.I.A.) or maximum interference volume (M.I.V.) would never be achieved because the internal peripheral side wall portions of the borehole would never be encountered by non-grooved, non-toothed, or non-threaded solid portions of the expansion sleeve component 14.

Thus, it may be seen that in accordance with the principles and teachings of the present invention, there has been disclosed a new and improved anchor assembly which comprises an axially oriented anchor bolt or threaded stud and an annularly grooved expansion sleeve or clip annularly disposed around the axially oriented anchor bolt or threaded stud wherein the annularly grooved expansion sleeve or clip has a continuous array of annularly oriented grooves, teeth, or threads, with the array comprising a predetermined number of grooves, threads, or teeth which are disposed about the forward end external peripheral surface portion of the expansion sleeve or clip so as not to extend throughout the entire axial length of the expansion sleeve or clip. In addition, the annularly grooved expansion sleeve or clip is fabricated from a metal sheet or plate which is formed into the annularly grooved expansion sleeve or clip so as to have a substantially C-shaped cross-sectional configuration that enables the annularly grooved expansion sleeve or clip to be expanded by effectively being opened as the axially oriented anchor bolt is pulled therethrough. In addition, each one of the annular teeth, threads, or grooves of the expansion clip or sleeve has a predetermined depth dimension, as measured between the root and crest portions thereof, that is larger than the distance that the cracked regions of the concrete block are opened during the cracked concrete testing technique or procedures so as to ensure the fact that the teeth, grooves, or threads of the expansion sleeve or clip effectively remain embedded within the side wall portions of the borehole formed within the concrete block during cracked concrete testing procedures or simulated environmental expansion and contraction conditions.

Still further, the internal peripheral surface portion of the annularly grooved expansion sleeve or clip, within the leading end portion thereof, and the external peripheral surface of the axially oriented anchor bolt, within the leading end portion thereof, have predetermined mating inclined slopes. All of these various features characteristic of the new and improved expansion sleeve or clip of the present invention effectively combine and contribute to the achievement of a maximum interference area (M.I.A.) or maximum interference volume (M.I.V.) as developed between the axially oriented anchor bolt and the annularly grooved expansion sleeve or clip, so as to, in turn, be developed between the annularly grooved expansion sleeve or clip and the internal peripheral side wall portions of the borehole formed within the concrete substrate or substructure so as to force the annularly grooved expansion clip or sleeve into its solidly affixed anchored disposition within a concrete borehole, to be formed within a concrete substrate or substructure, whereby the expansion sleeve or clip component will exhibit enhanced holding power and pull-out resistance properties.

Obviously, many variations and modifications of the present invention are possible in light of the above teachings. For example, the number of annular grooves, teeth, or threads, the number of threads per inch, the depth of the annular grooves, threads, or teeth, the particular angles of the mating inclined slopes of the forward, internal peripheral surface portion of the expansion sleeve component and the external peripheral surface portion of the frusto-conically configured wedge-type section of the head portion of the anchor bolt component, and the diameter of the anchor bolt or threaded stud, can be varied, the ultimate objective being the achievement of the maximum interference area (M.I.A.) and the maximum interference volume (M.I.V.) as defined between the anchor bolt component and the expansion sleeve component of the new and improved anchor bolt and expansion sleeve assembly, as well as between the expansion sleeve component and the internal peripheral side wall portions of the borehole defined within the concrete substructure or substrate. It is therefore to be understood that within the scope of the appended claims, the present invention may be practiced otherwise than as specifically described herein.

What is claimed as new and desired to be protected by Letters Patent of the United States of America, is:

1. A method of performing cracked concrete testing in a borehole, defined within a concrete substrate, using an anchor assembly, comprising the steps of:
providing a borehole within a concrete substrate;
anchoring an anchor assembly within said borehole defined within said concrete substrate so as to meet cracked concrete testing standards, wherein said anchor assembly comprises an anchor bolt member comprising a substantially cylindrical member formed about a longitudinal axis; an externally threaded load-application portion formed upon a rearward end portion of said anchor bolt member; an enlarged head member formed upon a forward end portion of said anchor bolt member and comprising an enlarged cylindrical portion and a frusto-conical portion integrally interconnecting said cylindrical portion of said enlarged head member to said cylindrically configured anchor bolt member, said frusto-conical portion having a predetermined radially outward angular inclination with respect to said longitudinal axis of said anchor bolt member as considered in the direction extending from said rearward end portion of said anchor bolt member toward said forward end portion of said anchor bolt member; an annular shoulder member integrally formed upon said anchor bolt member at a predetermined axial location upstream of said frusto-conical portion of said enlarged head member; and an expansion sleeve member annularly disposed about said anchor bolt member and having a substantially C-shaped cross-sectional configuration, defined around a longitudinal axis, so as to define an axial slit all along its axial extent, extending from a downstream end portion thereof to an upstream end portion thereof, so as to permit said expansion sleeve member to immediately open and expand radially outwardly, into engaged contact with interior wall portions of said borehole defined within said concrete substrate, when said anchor bolt member is pulled through said expansion sleeve member as a result of an application load being applied to said externally threaded load-application portion of said anchor bolt member, wherein an internal surface portion of said downstream end portion of said expansion sleeve member has a predetermined radially outward angular inclination with respect to said longitudinal axis of said expansion sleeve member, as considered in the direction extending from said rearward end portion of said anchor bolt member toward said forward end portion of said anchor bolt member, which is substantially the same as said angular inclination of said frusto-conical portion of said enlarged head member of said anchor bolt member such that said internal surface portion of said downstream end portion of said expansion sleeve member can be disposed in surface-to-surface contact with said frusto-conical portion of said enlarged head member of said anchor bolt member as a result of said upstream end portion of said expansion sleeve member being disposed in seated contact with said annular shoulder member of said anchor bolt member, and wherein further, a plurality of annular grooves are disposed only upon a forward external peripheral portion of said expansion sleeve member, while a rearward external peripheral portion of said expansion sleeve member is non-grooved and solid; and using a torquing assembly for imparting a predetermined torquing load to said anchor bolt member such that said enlarged head portion of said anchor bolt member expands said forward portion of said expansion sleeve member so that said plurality of annular grooves are forced into engagement with internal peripheral side wall portions of said borehole defined within said concrete substrate so as to define increased areas and volumes of interference with said internal peripheral side wall portions of said borehole defined within said concrete substrate, and is disposed entirely within the rearward portion of said expansion sleeve member so as to expand said rearward portion of said expansion sleeve member such that said non-grooved solid portion of said expansion sleeve member is forced into engagement with said internal peripheral side wall portions of said borehole defined within said concrete substrate so as to achieve, at said predetermined torquing load, a maximum interference area (M.I.A.) and maximum interference volume (M.I.V.) with said internal peripheral side wall portions of said borehole defined within said concrete substrate so as to enhance the holding power and pull-out resistance of said anchor assembly with respect to said borehole defined within said concrete substrate.

2. The method as set forth in claim 1, further comprising the step of:
forming said at least one cracked region within said concrete substrate by using crack initiators.

3. The method as set forth in claim 2, further comprising the step of:
selecting said crack initiators from the group comprising wedge-type devices, plates, and hydraulic expansion tubes.

4. The method as set forth in claim 1, further comprising the steps of:
providing rebars within said concrete substrate;
using a hydraulic pump as said component connected to said rebars of said concrete substrate; and
operatively connecting said hydraulic pump to said rebars of said concrete substrate by hydraulic connectors.

5. The method as set forth in claim 1, further comprising the step of:
using a linearly variable displacement transformer (LVDT) to measure said movement of said anchor bolt assembly within said at least one cracked region of said concrete substrate, while said at least one cracked region of said concrete substrate is being cyclically expanded and contracted between said OPENED and CLOSED positions, so as to effectively gauge the pull-out resistance of said anchor bolt assembly with respect to said concrete substrate.

6. The method as set forth in claim 1, further comprising the step of:
providing the number of said plurality of annular grooves, disposed upon said forward external peripheral portion of said expansion sleeve member, within the range of three to eight.

7. The method as set forth in claim 1, further comprising the step of:
providing the plurality of annular grooves, disposed upon said forward external peripheral portion of said expansion sleeve member, with a predetermined pitch defined between successive adjacent grooves as based upon the number of grooves per inch which is within the range of twenty to thirty-two grooves per inch.

8. The method as set forth in claim 1, further comprising the step of:
providing all of said plurality of annular grooves, disposed upon said forward external peripheral portion of said expansion sleeve member, with a depth dimension which is within the range of 0.015-0.050 inches (0.015-0.050").

9. The method as set forth in claim 8, further comprising the step of:
providing all of said plurality of annular grooves, disposed upon said forward external peripheral portion of said expansion sleeve member, with the same depth dimension which is within the range of 0.015-0.050 inches (0.015-0.050").

10. The method as set forth in claim 8, further comprising the step of:

providing all of said plurality of annular grooves, disposed upon said forward external peripheral portion of said expansion sleeve member, with different depth dimensions within said range of 0.015-0.050 inches (0.015-0.050").

11. The method as set forth in claim 1, further comprising the step of:

providing a forward, internal peripheral surface portion of said expansion sleeve member, and an external peripheral surface portion of said anchor bolt member, with substantially matching angular orientations as considered with respect to said longitudinal axis of said anchor bolt member.

12. The method as set forth in claim 11, further comprising the step of:

providing said substantially matching angular orientations of said forward, internal peripheral surface portion of said expansion sleeve member, and said external peripheral surface portion of said anchor bolt member, as being approximately 10°.

13. The method as set forth in claim 1, further comprising the step of:

providing said annular expansion sleeve member, disposed around said anchor bolt member, as a sheet member rolled upon itself so as to have a substantially C-shaped cross-sectional configuration.

14. The method as set forth in claim 13, further comprising the step of:

fabricating said annular expansion sleeve member from metal.

15. The method as set forth in claim 14, further comprising the step of:

fabricating said annular metal expansion sleeve member from low-carbon steel plated with zinc.

16. The method as set forth in claim 14, further comprising the step of:

fabricating said annular metal expansion sleeve member from carbon-steel plated with a zinc-tin composition.

17. The method as set forth in claim 1, further comprising the steps of:

providing said expansion sleeve member, annularly disposed around said anchor bolt member, with a rearwardly disposed body portion having a predetermined external diametrical extent; and forming said plurality of annular grooves, disposed only upon said forward external peripheral portion of said expansion sleeve member, such that said plurality of annular grooves do not extend radially beyond said external diametrical extent of said rearwardly disposed body portion of said expansion sleeve member so as not to gouge internal peripheral side wall portions of the borehole defined within the substrate during installation of said anchor assembly into the borehole defined within the substrate.

18. The method as set forth in claim 1, further comprising the step of:

providing barbs upon said expansion sleeve member, annularly disposed upon said anchor bolt member, for effectively biting into, and becoming embedded within, internal peripheral surface portions of the concrete wall defining said borehole within said concrete substrate so as to thereby prevent rotation of said expansion sleeve component with respect to said borehole defined within said concrete substrate.

19. The method as set forth in claim 18, further comprising the step of:

providing said barbs as a plurality of barbs circumferentially spaced upon said expansion sleeve member annularly disposed upon said anchor bolt member.

20. The method as set forth in claim 19, further comprising the step of:

forming each one of said plurality of barbs such that each one of said plurality of barbs has a substantially triangular configuration.

21. The method as set forth in claim 19, further comprising the step of:

forming each one of said plurality of barbs such that each one of said plurality of barbs has a primary longitudinal axis which is disposed substantially parallel to said longitudinal axis of said expansion sleeve member.

22. The method as set forth in claim 19, further comprising the step of:

forming each one of said plurality of barbs such that each one of said plurality of barbs has a primary longitudinal axis which is disposed at a predetermined angle with respect to said longitudinal axis of said expansion sleeve member.

23. The method as set forth in claim 22, further comprising the step of:

forming each one of said plurality of barbs such that said predetermined angle, at which each one of said plurality of barbs is angularly offset with respect to said longitudinal axis of said expansion sleeve member, is approximately 20°.

\* \* \* \* \*